(12) United States Patent
Argentine

(10) Patent No.: US 9,486,350 B2
(45) Date of Patent: Nov. 8, 2016

(54) STENT-GRAFT DELIVERY SYSTEM HAVING HANDLE MECHANISM FOR TWO-STAGE TIP RELEASE

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 291 days.

(21) Appl. No.: 14/230,826

(22) Filed: Mar. 31, 2014

(65) Prior Publication Data
US 2015/0272759 A1  Oct. 1, 2015

(51) Int. Cl.
*A61F 2/966* (2013.01)
*A61F 2/95* (2013.01)

(52) U.S. Cl.
CPC ........ *A61F 2/966* (2013.01); *A61F 2002/9517* (2013.01); *A61F 2002/9665* (2013.01)

(58) Field of Classification Search
CPC .. A61F 2/966; A61F 2002/9517; A61F 2/95; A61F 2002/9665; A61F 2/962; A61F 2002/0072; A61F 2002/2484; A61F 2/2466; A61F 2002/4623; A61F 2002/9528; A61F 2002/9534; A61F 2002/30525; A61B 1/00066; A61B 1/0052; A61M 5/31581; A61M 25/0631
USPC .......................................................... 623/1.1
See application file for complete search history.

(56) References Cited

U.S. PATENT DOCUMENTS

| 7,264,632 | B2 | 9/2007 | Wright et al. |
| 8,663,302 | B2 | 3/2014 | Schmitt et al. |
| 2008/0228255 | A1 | 9/2008 | Rust et al. |
| 2013/0274859 | A1 | 10/2013 | Argentine |
| 2013/0274860 | A1 | 10/2013 | Argentine |

*Primary Examiner* — Eric Rosen
*Assistant Examiner* — George J Ulsh

(57) ABSTRACT

A delivery system for a stent-graft is disclosed having a tip capture device and a tip release handle mechanism configured to actuate the tip capture device. The tip release handle mechanism includes a rotatable grip component and a tip release actuation component. The grip component may be rotatable in a first direction to transition a proximal stent of the stent-graft from the delivery state to a partially deployed state and rotatable in an opposite, second direction to transition the proximal stent from the partially deployed state to a fully deployed state. The grip component is operably coupled to the tip release actuation component. The delivery system further includes a shaft component operably coupled to the tip release actuation component and the tip capture device.

20 Claims, 12 Drawing Sheets

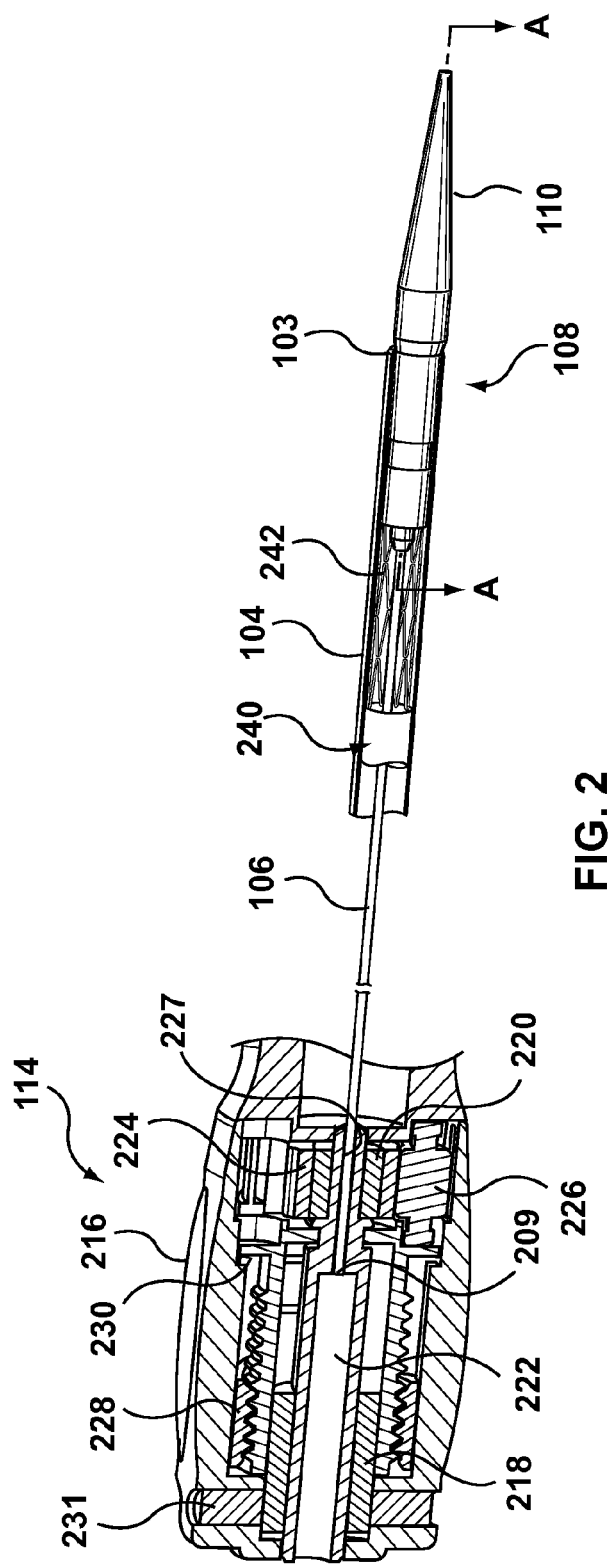
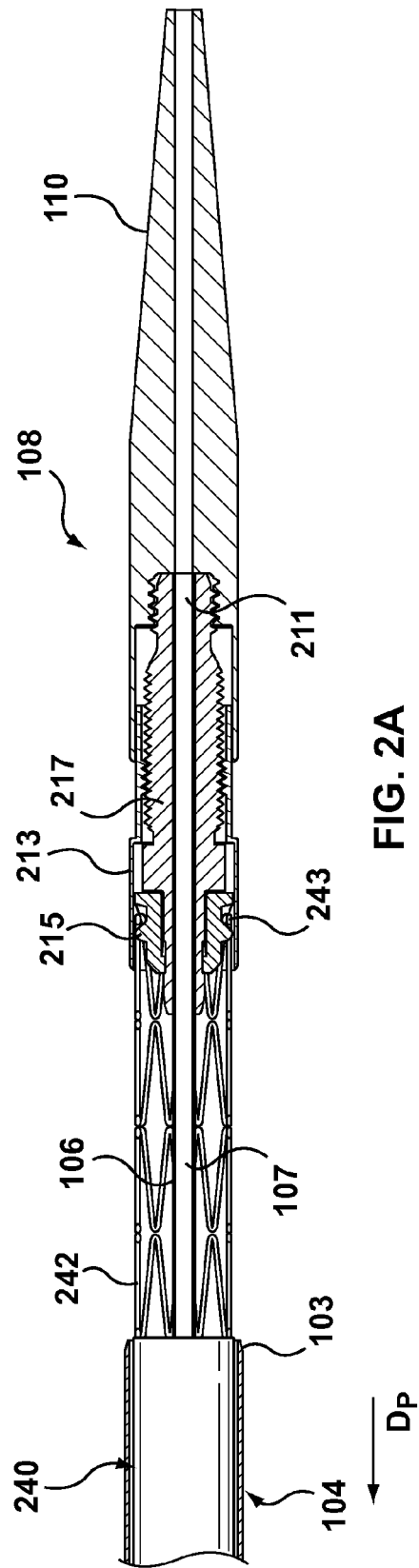
FIG. 2
FIG. 2A

STENT-GRAFT DELIVERY SYSTEM HAVING HANDLE MECHANISM FOR TWO-STAGE TIP RELEASE

FIELD OF THE INVENTION

The invention relates to a catheter-based delivery system for deploying a prosthesis within the vasculature and, more particularly, to a tip release handle mechanism for the catheter-based delivery system that provides a two-stage tip release of the prosthesis.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable biocompatible material in its intended position within the blood vessel. Most commonly, the graft anchoring component is one or more radially compressible stents that are radially expand in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Tubular grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

Specialized endovascular stent-grafts have been developed for the treatment of abdominal aortic aneurysm, hereinafter referred to as an AAA. An AAA is a bulge that forms in the wall of the abdominal aorta, which is the main vessel of the arterial system of the body that extends through the abdomen. An endovascular stent-graft for use in the abdominal aorta typically includes a number of self-expanding stent-graft segments that are assembled or mated within the patient to provide the finished stent-graft implant. The stent-graft implant may include a main stent-graft segment that constitutes a trunk section with two descending limb sections with the limb sections providing an anchoring point for subsequent endovascular placement of a right iliac limb stent-graft segment and a left iliac limb stent-graft segment of the stent-graft implant. Typically, the main stent-graft segment is delivered and implanted via a main delivery system that is withdrawn prior to respective branch delivery systems being introduced for delivery and implantation of each of the iliac limb stent-graft segments.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed in a delivery configuration within a distal end of the outer tube or sheath of the delivery catheter. The delivery catheter may then be tracked through the vasculature until the distal end of the delivery catheter and the stent-graft disposed therein reach a treatment site. At least a proximal stent of the stent-graft is then released from the confines of the outer sheath and permitted to self-expand into apposition with the surrounding tissue of the vessel in order to anchor the stent-graft therein. It is beneficial in most procedures if the position of the proximal stent of the stent-graft is confirmed prior to full deployment in order to permit slight adjustments in the positioning thereof, if necessary. Accordingly some clinicians attempt to partially deploy or "flower" the proximal stent to assure proper positioning thereof before final release within the vasculature. However in known stent-graft delivery systems there is little certainty for the clinician in determining at which point during deployment the proximal stent may be partially deployed, or "flowered," rather than fully deployed and released from the delivery system. Thus a need in the art exists for an improved stent-graft delivery system that consistently and reliably permits partial deployment or "flowering" of a proximal stent of a stent-graft in order to assure proper positioning thereof prior to full deployment or release of the proximal stent of the stent-graft.

BRIEF SUMMARY OF THE INVENTION

A delivery system for a stent-graft is disclosed having a tip capture device for holding a proximal stent of the stent-graft in a delivery state and a handle mechanism configured to actuate the tip capture device to deploy the proximal stent of the stent-graft in two stages. The handle mechanism includes a rotatable grip component and a tip release actuation component. The grip component may be rotatable in a first direction to transition the proximal stent from the delivery state to a partially deployed state and may be rotatable in an opposite, second direction to transition the proximal stent from the partially deployed state to a fully deployed state. The tip release actuation component may be operably coupled to the grip component such that the rotation of the grip component in each of the first and second directions rotates the tip release actuation component in the first direction. The delivery system further includes a shaft component having a proximal end operably coupled to the tip release actuation component and a distal end operably coupled to the tip capture device.

A delivery system for a stent-graft is disclosed having a tip capture device for holding a proximal stent of the stent-graft in a delivery state and a handle mechanism configured to actuate the tip capture device to deploy the proximal stent of the stent-graft in two stages. The handle mechanism includes a rotatable grip component, a tip release actuation component and a stop component. The grip component may be rotatable in a first direction to partially release the proximal stent from the tip capture device such that the proximal stent transitions from the delivery state to a partially deployed state, and may be rotatable in an opposite second direction to fully release the proximal stent from the tip capture device such that the proximal stent transitions from the partially deployed state to a fully deployed state. The tip release actuation component for actuating the tip capture device may be operably coupled to the grip component such that rotation of the grip component in the first direction rotates the tip release actuation component in the first direction to position the tip capture device for partial release of the proximal stent and such that rotation of the grip component in the second direction rotates the tip release actuation component in the first direction to position the tip capture device for full release of the proximal stent. The stop component may be distally translated relative to the grip component by rotation of the grip component in the first direction and may be proximally translated relative to the grip component by rotation of the grip component in the second direction, wherein when the distally translated stop component contacts a hard stop of the handle mechanism the grip component is prevented from further rotation in the first direction and the proximal stent of the stent-graft is in the partially deployed state.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1A is a cross-sectional view of the delivery system of FIG. 1 taken along line A-A thereof.

FIG. 2 depicts a sectional view of a tip release handle mechanism attached to an inner shaft and a tip capture device of the delivery system of FIG. 1.

FIG. 2A is an enlarged sectional view of the tip capture device of FIG. 2 taken along line A-A thereof, with a portion of a stent-graft shown in a compressed, delivery state.

DETAILED DESCRIPTION OF THE INVENTION

Specific embodiments of the present invention are now described with reference to the figures, wherein like reference numbers indicate identical or functionally similar elements. Regarding "proximal" and "distal" positions referenced herein, a proximal end of a prosthesis, e.g., stent-graft, is the end closest to the heart by way of blood flow path whereas a distal end of the prosthesis is the end furthest away from the heart during deployment. In contrast, a distal end of the stent-graft delivery system or other associated delivery apparatus is usually identified as the end that is farthest from the operator, while a proximal end of the delivery system and devices is the end nearest the operator or handle of the catheter. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of embodiments hereof is in the context of treatment of abdominal aortic aneurysms (AAA), the invention may also be adapted for use in other procedures where it may be deemed useful. Furthermore, there is no intention to be bound by any expressed or implied theory presented in the preceding technical field, background, brief summary or the following detailed description.

Figure 1:
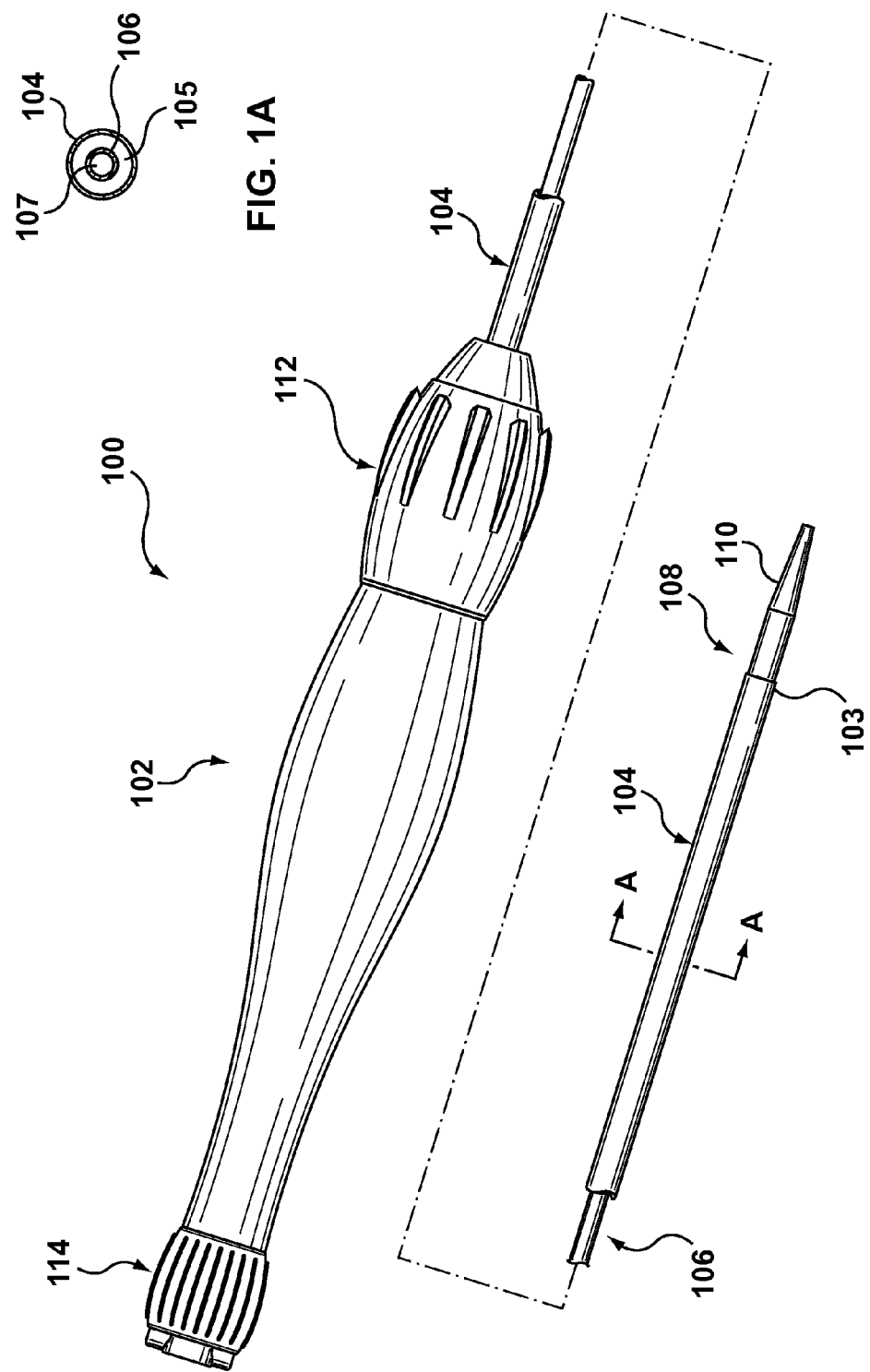
FIG. 1 is a perspective view of a stent-graft delivery system in accordance with an embodiment hereof.

FIG. 1 is a perspective view of a delivery catheter 100 for a self-expanding stent-graft prosthesis in accordance with an embodiment hereof, with FIG. 1A being a cross-sectional view of delivery catheter 100 taken along line A-A of FIG. 1. In an embodiment, the self-expanding stent-graft prosthesis is a main stent-graft segment for use in treating an AAA. Delivery catheter 100 may also be referred to as a stent-graft delivery system. Delivery catheter 100 includes a handle 102, an elongate outer shaft or tubular component 104, an elongate inner shaft or tubular component 106 and a tip capture device 108, which defines a distal tip 110 of the catheter. Outer shaft 104 defines a lumen 105 from a proximal end (not shown) to a distal end 103 thereof, and may alternatively be referred to herein as a sheath. The proximal end of outer shaft 104 is operably coupled to a sheath retraction mechanism 112 of handle 102 and, in a delivery configuration, distal end 103 of outer shaft 104 abuts with tip capture device 108, such that together outer shaft 104 and tip capture device 108 hold a stent-graft in a compressed delivery configuration within a distal portion of delivery catheter 100. During deployment of the stent-graft, sheath retraction mechanism 112 is rotated in order to proximally retract outer shaft 104 to thereby incrementally expose the stent-graft and, once the stent-graft is properly positioned, to permit the full release of the self-expanding stent-graft from delivery catheter 100, as explained in more detail below.

Inner shaft 106 extends within lumen 105 of outer shaft 104 and defines a lumen 107 from a proximal end 209 to a distal end 211 thereof. In an embodiment, lumen 107 is sized to receive a guidewire therethrough. FIG. 2 depicts a sectional view of a tip release handle mechanism 114 of handle 102 attached to proximal end 209 of inner shaft 106 with tip capture device 108 being attached to distal end 211 of inner shaft 106. For ease of illustration a remainder of delivery catheter 100 is removed from FIG. 2 with a portion of a stent-graft 240 being shown in a compressed, delivery configuration within a distal portion of outer shaft 104. FIG. 2A is an enlarged sectional view taken along line A-A of FIG. 2 that depicts tip capture device 108 with a self-expanding proximal stent 242 of stent-graft 240 held in a compressed, delivery state. Proximal tips or apices 243 of proximal stent 242 are held between a sleeve 213 and a spindle 215 of tip capture device 108. Sleeve 213 is threadably engaged with a threaded transmission component 217 that surrounds and is fixed to a distal portion of inner shaft 106 to rotate therewith, such that sleeve 213 is operably coupled to inner shaft 106 to be distally advanced thereby. In an embodiment, tip release handle mechanism 114 is operably coupled to tip capture device 108 such that rotation of inner shaft 106 in a first direction moves or distally advances sleeve 213 relative to spindle 215 and proximal stent 242 in two distinct steps or stages, wherein during a first step or stage the proximal tips 243 are partially uncovered and during a second step or stage the proximal tips 243 are fully uncovered and released from tip capture device 108. It would be understood by one of ordinary skill in the art that a tip capture device may incorporate other mechanisms or components than those shown in the current embodiment to convert a rotational force of shaft 106 into a longitudinal translation of sleeve 213 without departing from the scope of the present invention. For example, tip capture devices as shown and described in U.S. Pat. Appl. Pub. No. 2013/0274859 to Argentine and U.S. Pat. Appl. Pub. No. 2013/0274860 to Argentine, each of which is incorporated by reference herein in its entirety, may be adapted for use in embodiments hereof.

Figure 3A:
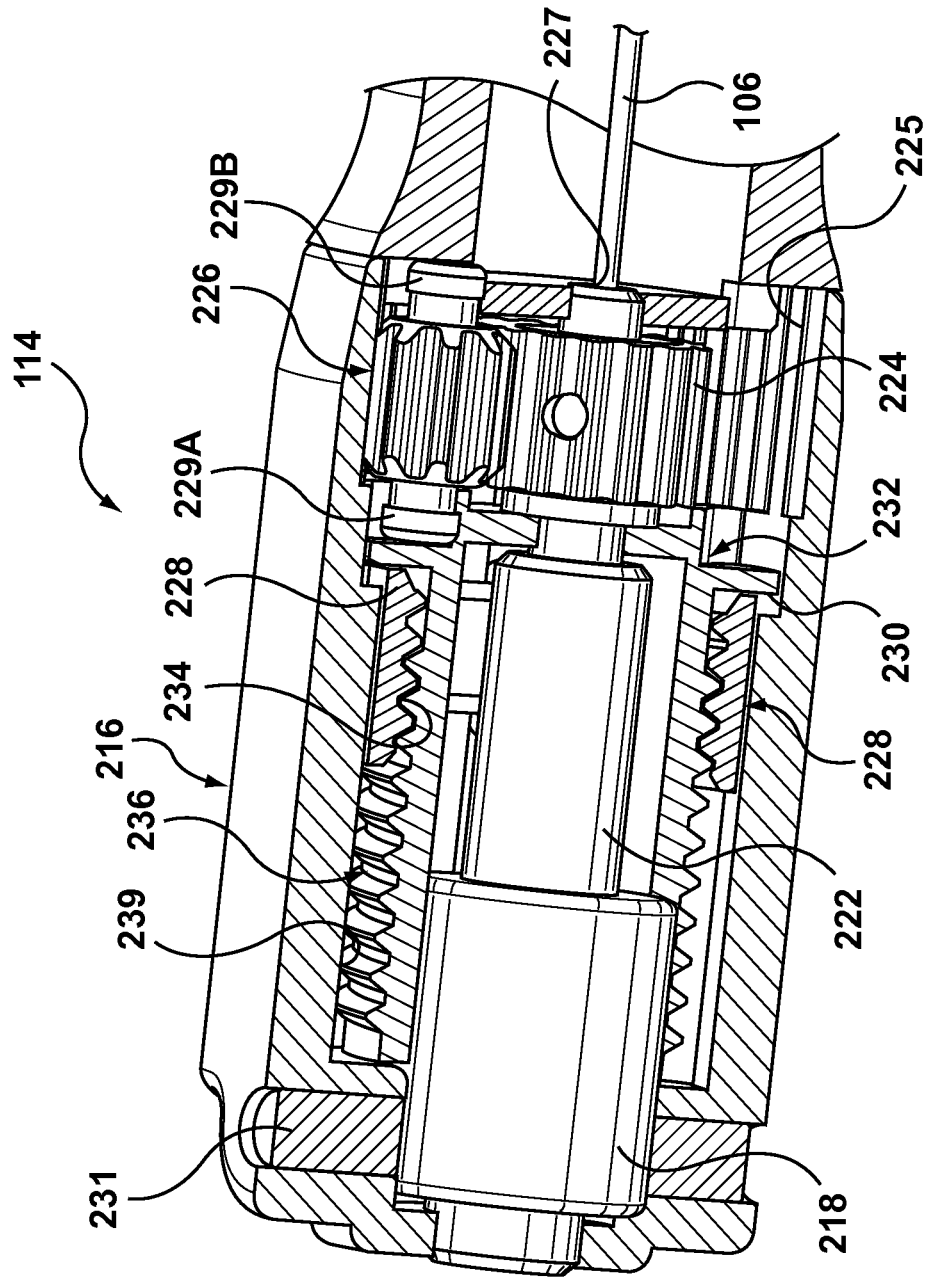
FIG. 3A is an alternate sectional view of the tip release handle mechanism of FIG. 1.

With reference to FIGS. 2 and 3A, tip release handle mechanism 114 includes a rotatable grip component 216 that is operably coupled to a proximal portion of inner shaft 106 by a proximal one-way bearing 218, a distal one-way bearing 220, a tip release or inner shaft actuation component 222, and first and second gears 224, 226. The tip release handle mechanism 114 also includes a stop component 228 that is longitudinally translatable by grip component 216. Briefly, rotation of grip component 216 in each of a first and second direction rotates the inner shaft 106 in the first direction, which causes distal advancement of sleeve 213 of tip capture device 108 to provide the two stage release of proximal tips 243 of proximal stent 242 of the stent-graft 240, as described in more detail below. Rotation of grip component 216 in the first direction concurrently longitudinally translates stop component 228 in a distal direction until stop component 228 contacts a hard stop 230 of handle housing 232, as shown in FIG. 3A. Hard stop 230 is spaced from a proximal end of grip component 216 by threaded track 236. The contact of stop component 228 with hard stop 230 prevents further rotation of the grip component 216 in the first direction, as stop component 228 can no longer move in the distal direction. Thereafter rotation of grip component 216 may continue only in the second direction, which longitudinally translates stop component 228 in a proximal direction while maintaining rotation of inner shaft 106 in the first direction to thereby continue the distal advancement of sleeve 213. In embodiments hereof, the first direction may be either clockwise or counterclockwise with the second direction being the opposite direction thereof.

Figure 3B:
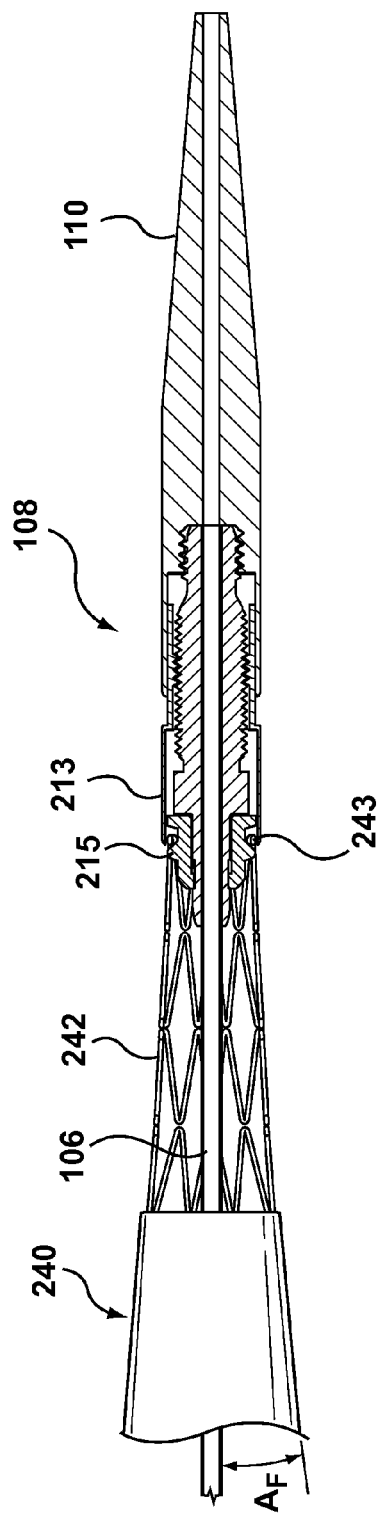
FIG. 3B is the tip capture device as shown in FIG. 2 with a proximal stent of the stent-graft partially deployed.
Figure 4:
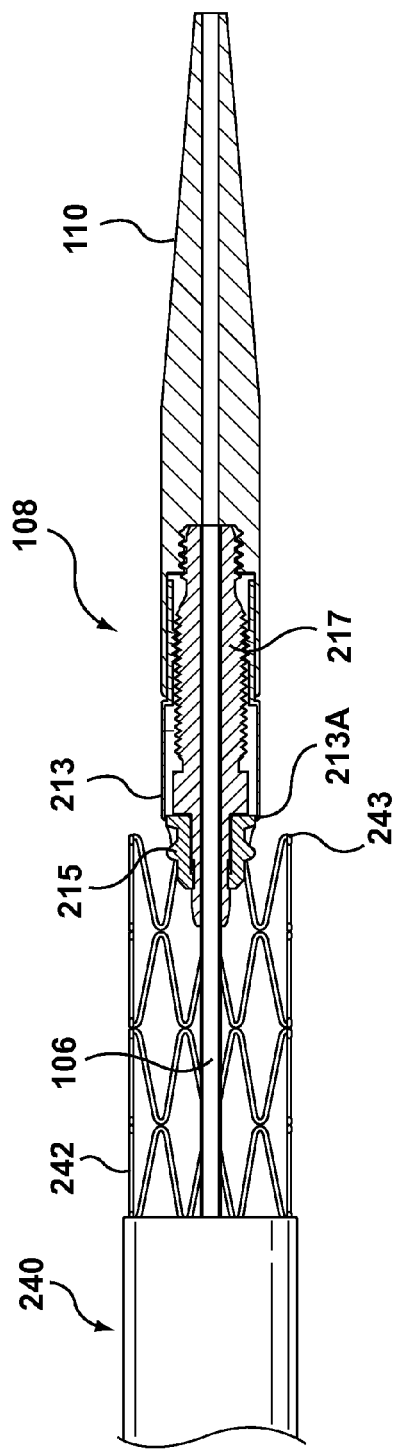
FIG. 4 is the tip capture device as shown in FIG. 2 with the proximal stent of the stent-graft fully deployed.

With reference to FIGS. 1 and 2A, when stent-graft 240 held in a delivery configuration by delivery catheter 100 is to be deployed, sheath retraction mechanism 112 is rotated to retract outer tube or sheath 104 in a proximal direction, as represented by arrow $D_P$ in FIG. 2A, such that distal end 103 is disposed proximal of proximal stent 242 of stent-graft 240. Grip component 216 is then rotated in the first direction to rotate inner shaft 106 in the first direction to thereby distally advance sleeve 213 relative to proximal tips 243 of self-expanding proximal stent 242. While grip component 216 is rotated in the first direction stop component 228 is distally advanced thereby until stop component 228 contacts hard stop 230, as shown in FIG. 3A, which prevents further rotation of grip component 216 in the first direction. The first stage of tip release has been performed when grip component 216 can no longer be rotated in the first direction, wherein sleeve 213 of tip capture device 108 will have been distally advanced a sufficient distance to partially uncover proximal tips 243, as shown in FIG. 3B, which permits self-expanding proximal stent 242 to transition from a delivery state to a partially deployed state. With the proximal tips 243 partially uncovered but still attached to tip capture device 108, the remainder of proximal stent 242 will expand outward at an angle $A_F$ from inner shaft 106. In embodiments hereof, angle $A_F$ may be in the range of 10° to 40°. Proximal stent 106 may be described as "flowered" at this point in the procedure. With the proximal stent "flowered" in the partially deployed state, a clinician via fluoroscopy may assure proper positioning at a treatment site of proximal stent 242 before full deployment of stent-graft 240. Accordingly, if proximal stent 242 is found to be not properly positioned at this stage of the procedure, the clinician may "push" or otherwise manipulate the proximal stent until proper placement is confirmed. Thereafter sheath retraction mechanism 112 is rotated to continue proximal retraction of outer tube or sheath 104 until the remainder of stent-graft 240 is completely uncovered, and thus allowed to release or deploy from delivery catheter 100. Grip component 216 is then rotated in the second direction to proximally translate stop component 228 and continue rotation of inner shaft 106 in the first direction to thereby resume distal advancement of sleeve 213. With reference to FIG. 4, grip component 216 is rotated in the second direction until at least a distal edge 213A of sleeve 213 is distal of proximal tips 243 of proximal stent 242. Once sleeve 213 of tip capture device 108 is distal of proximal tips 243, the second stage of tip release has been performed, wherein proximal tips 243 release from or move free of tip capture device 108 and self-expanding proximal stent 242 transitions from the partially deployed state to a fully deployed state. With the release of proximal stent 242 from tip capture device 108, the stent-graft 240 is fully deployed.

Figure 5A:
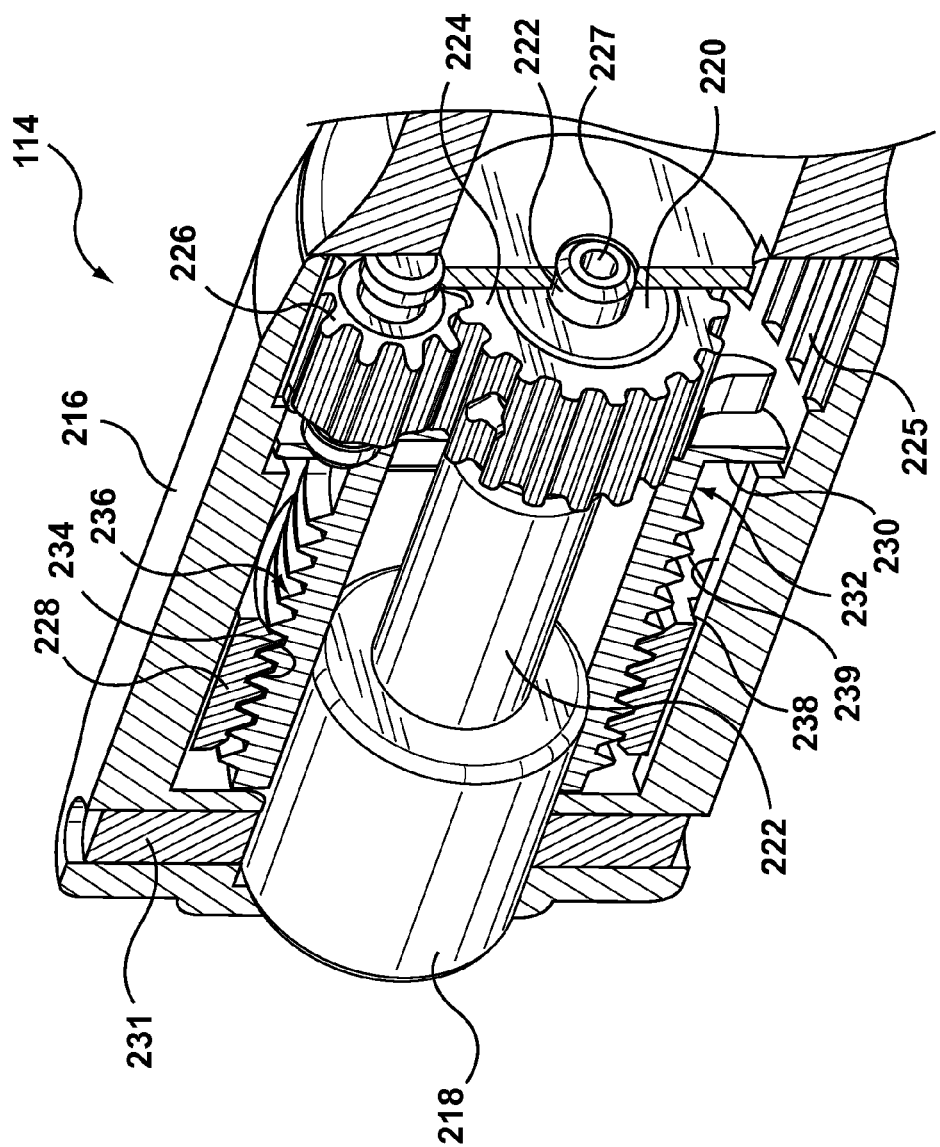
FIGS. 5A, 5B and 5C are alternate views of the tip release handle mechanism of FIG. 1.
Figure 5B:
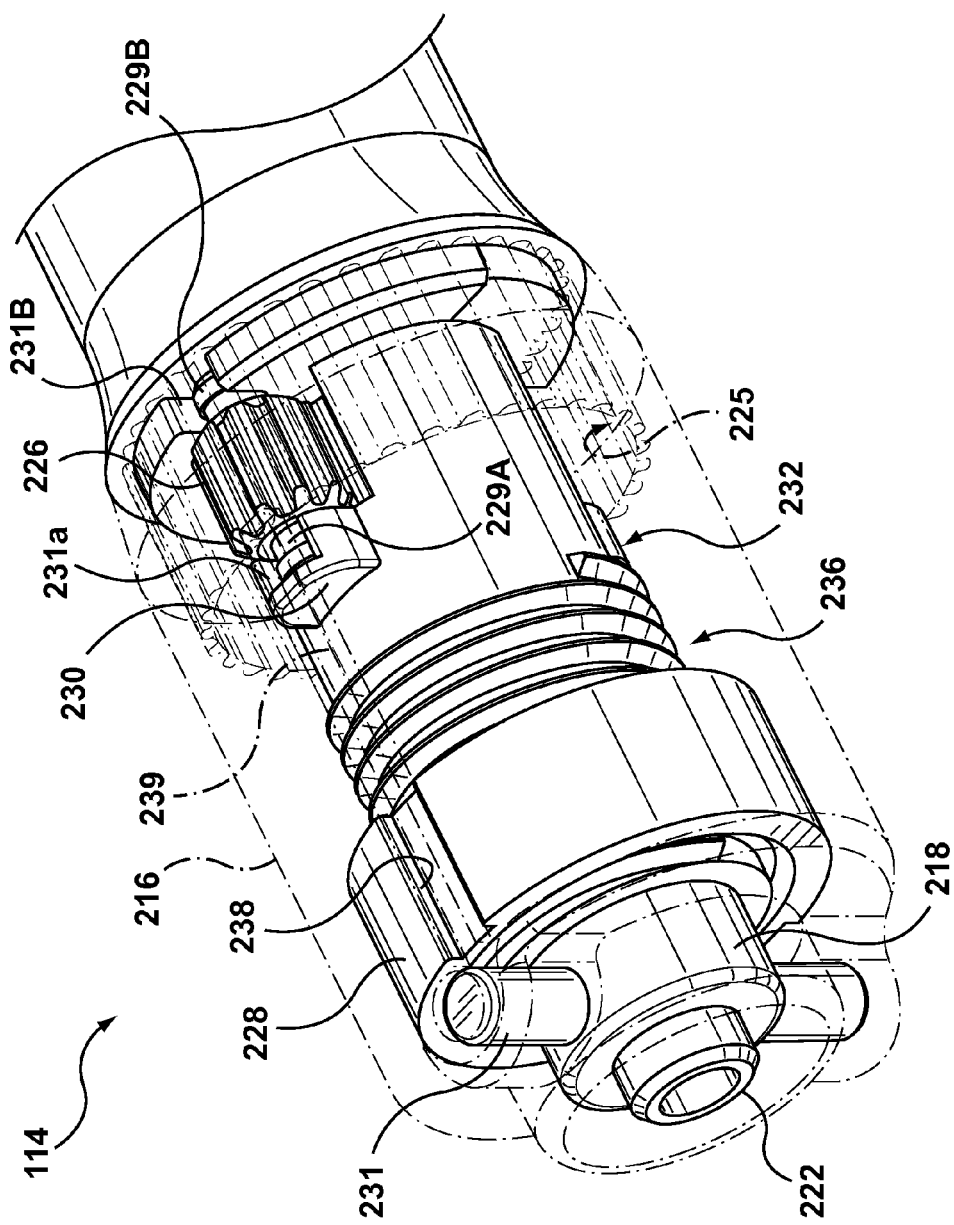
Figure 5C:
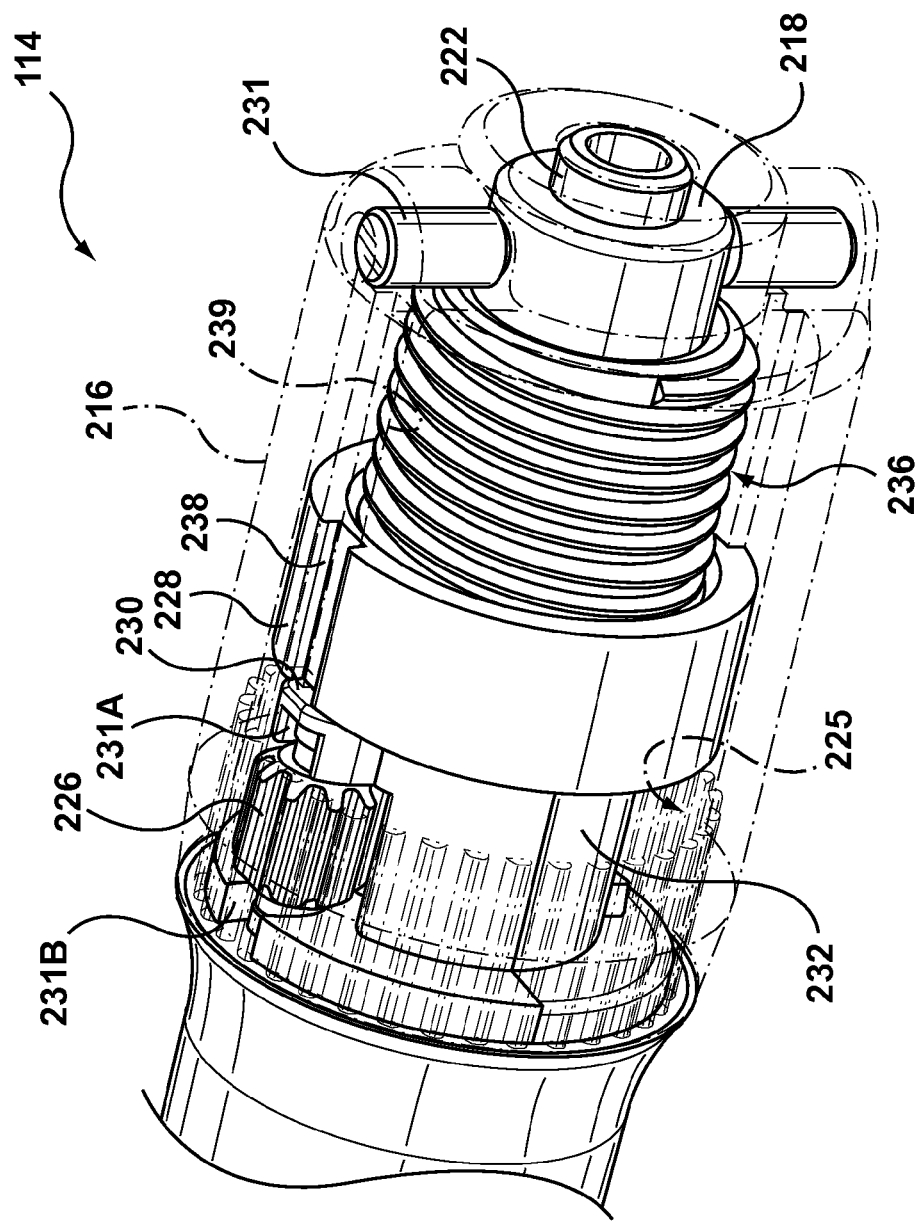

The mechanical interaction of the various components of tip release handle mechanism 114 will now be discussed in detail herein with reference to FIGS. 3A, 5A, 5B and 5C. FIG. 5A is an alternate sectional view of tip release handle mechanism 114 with inner shaft 106 removed, and FIGS. 5B and 5C are perspective views of tip release handle mechanism 114 in which grip component 216 is shown in phantom. Tip release handle mechanism 114 utilizes proximal and distal one-way bearings 218, 220 to transfer a rotational force from grip component 216 to tip release actuation component 222. Essentially a one-way bearing acts as a bearing in only one direction to permit rotation of a mechanism on which it is mounted in only one direction. Such a one-way bearing may also be referred to as a clutch bearing or a sprag clutch. In embodiments hereof, each of proximal and distal one-way bearings 218, 220 may consist of an outer tubular part or casing that holds within it an inner part or cage that functions as a retaining, limiting and locking mechanism for a plurality of rollers and springs. The rollers may be hard cylindrical pins that provide a smooth, consistent rolling surface for contact with an outer surface of tip release actuation component 222 on which proximal and distal one-way bearings 218, 220 are operably secured. In an embodiment, each of proximal and distal one-way bearings 218, 220 are tightly fit onto respective proximal and distal portions of tip release actuation component 222 with a proximal portion of inner shaft 106 being fixed within a receiving bore 227 of tip release actuation component 222, such as by bonding, laser-welding or using an adhesive. When the outer tubular part of a respective proximal or distal one-way bearing 218, 220 is rotated in the first direction, the rollers are positioned away from the springs and cannot rotate as they become lodged between the inner cage and the outer surface of the tip release actuation component 222, which effectively locks the respective proximal or distal one-way bearing 218, 220 against tip release actuation component 222 to thereby transfer a rotational force in the first direction to tip release actuation component 222 and inner shaft 106 held therein. When the outer tubular part of the respective proximal or distal one-way bearing 218, 220 is rotated in the second direction, the rollers are positioned against the springs thereby experiencing no load and freely rolling on the outer surface of tip release actuation component 222, such that the respective proximal or distal one-way bearing 218, 220 spins freely or idles with respect to tip release actuation component 222.

Grip component 216 is attached by set screws 231 to proximal one-way bearing 218, which surrounds and is secured to the proximal portion of tip release actuation component 222. Grip component is also operably coupled via first gear 224 and second gear 226 to distal one-way bearing 220, with distal one-way bearing 220 surrounding and being secured to the distal portion of tip release actuation component 222. In embodiments hereof, first gear 224 may be referred to as a sun gear and second gear 226 may be referred to as a pinion gear. Second gear 226 has hubs 229A, 229B at either end thereof that are rotatably received within corresponding casings 231A, 231B formed within a portion of handle housing 232. Second gear 226 is positioned between grip component 216 and first gear 224 to mesh with or engage each of an annular or ring gear 225, which is formed to inwardly extend from an interior surface of grip component 216, and first gear 224, which surrounds and is secured to distal one-way bearing 220.

As previously noted, grip component 216 of handle mechanism 114 is operably coupled to inner shaft 106 in such a manner that when grip component 216 is rotated in each of the first and second directions, tip release actuation component 222 and inner shaft 106 rotate in the first direction. In order for the tip release handle mechanism 114 to operate in this manner, the rotation of grip component 216 in the first direction causes the outer tubular part of proximal one-way bearing 218 to rotate in the first direction such that the proximal one-way bearing 218 locks onto tip release actuation component 222 to transfer the rotational force in the first direction thereto. Concurrently, the rotation of grip component 216 in the first direction causes the outer tubular part of distal one-way bearing 220 to rotate in the second direction to idle distal one-way bearing 220 which is due to the transfer of the rotational force thereto by the interaction of second gear 226 with first gear 224 and annular gear 225. More particularly during rotation of grip component 216 in the first direction, the second or pinion gear 226 is rotated by annular or ring gear 225 of grip component 216 in the first direction while meshing with and thereby rotating first or sun gear 226 in the opposite, second direction, which in turn rotates the outer tubular part of distal one-way bearing 220 in the second direction such that the distal one-way bearing is idle.

Conversely, the rotation of grip component 216 in the second direction causes the outer tubular part of proximal one-way bearing 218 to rotate in the second direction such that the proximal one-way bearing idles. Concurrently, the rotation of grip component 216 in the second direction causes the outer tubular part of distal one-way bearing 220 to rotate in the first direction such that the distal one-way bearing 220 locks onto tip release actuation component 222 and transfers the rotational force in the first direction thereto. More particularly during rotation of grip component 216 in the second direction, the second or pinion gear 226 meshes with annular gear 225 of grip component 216 to rotate therewith in the second direction while meshing with and thereby rotating first or sun gear 224 in the opposite, first direction, which in turn rotates the outer tubular part of distal one-way bearing 220 in the first direction to lock the distal one-way bearing 220 onto tip release actuation component 222 and to transfer the rotational force in the first direction thereto.

The operation of stop component 228 will now be more fully described with reference to FIGS. 3A, 5A, 5B and 5C. Stop component 228 has an annular shape with a threaded bore 234 for engaging with and translating along complementary threaded track 236, which is formed within handle housing 232. Stop component 228 also includes one or more longitudinally-extending grooves or channels 238 formed in an outer surface thereof, each of which slidably engages with a complimentary longitudinally-extending rail or protrusion 239 of grip component 216. The one or more rails 239 are formed to inwardly extend from the interior surface of grip component 216. Accordingly when grip component 216 is rotated in one of the first and second directions, the engagement of rails 239 with respective channels 238 of stop component 228 results in the corresponding rotation of stop component 228 along threaded track 236 in the first or second direction such that the stop component 228 axially slides along rails 239 of grip component 216 to move distally or proximally relative thereto. In an embodiment as described above, stop component 228 is distally translatable relative to grip component 216 when the grip component is rotated in the first direction and is proximally translatable relative to grip component 216 when the grip component is rotated in the second direction.

Figure 6:
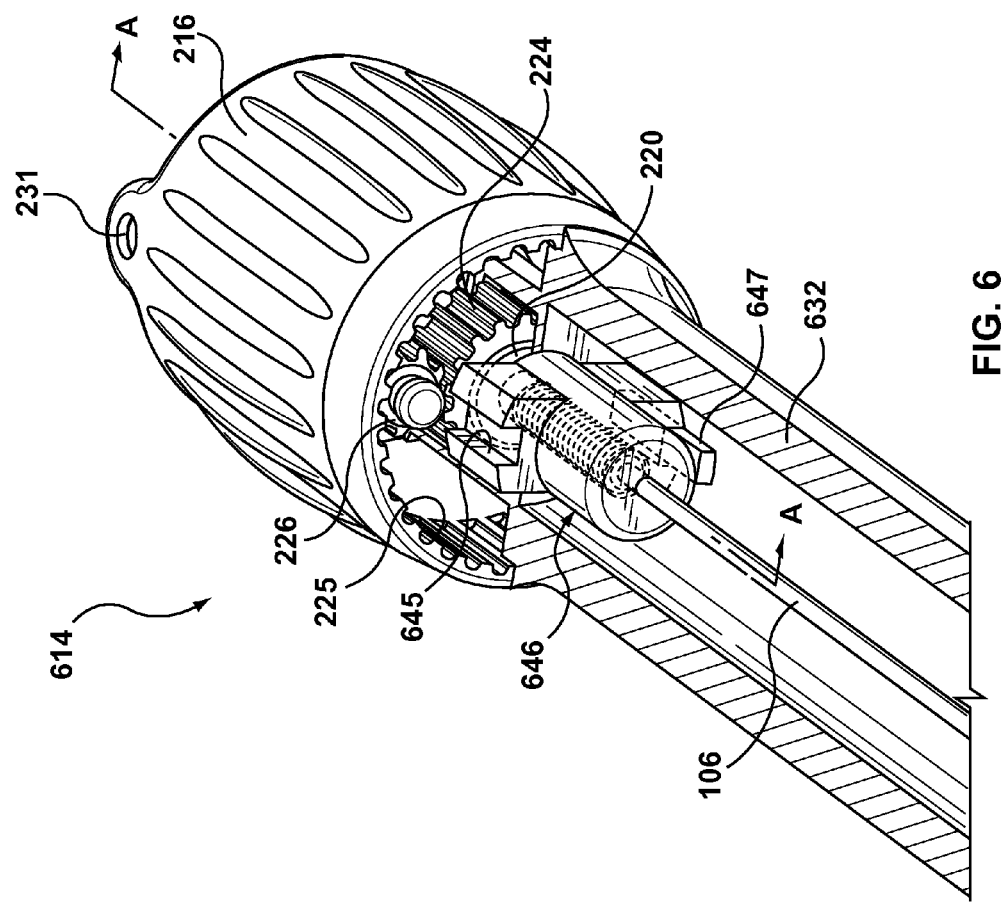
FIG. 6 is a perspective view of a tip release handle mechanism in accordance with another embodiment hereof.
Figure 6A:
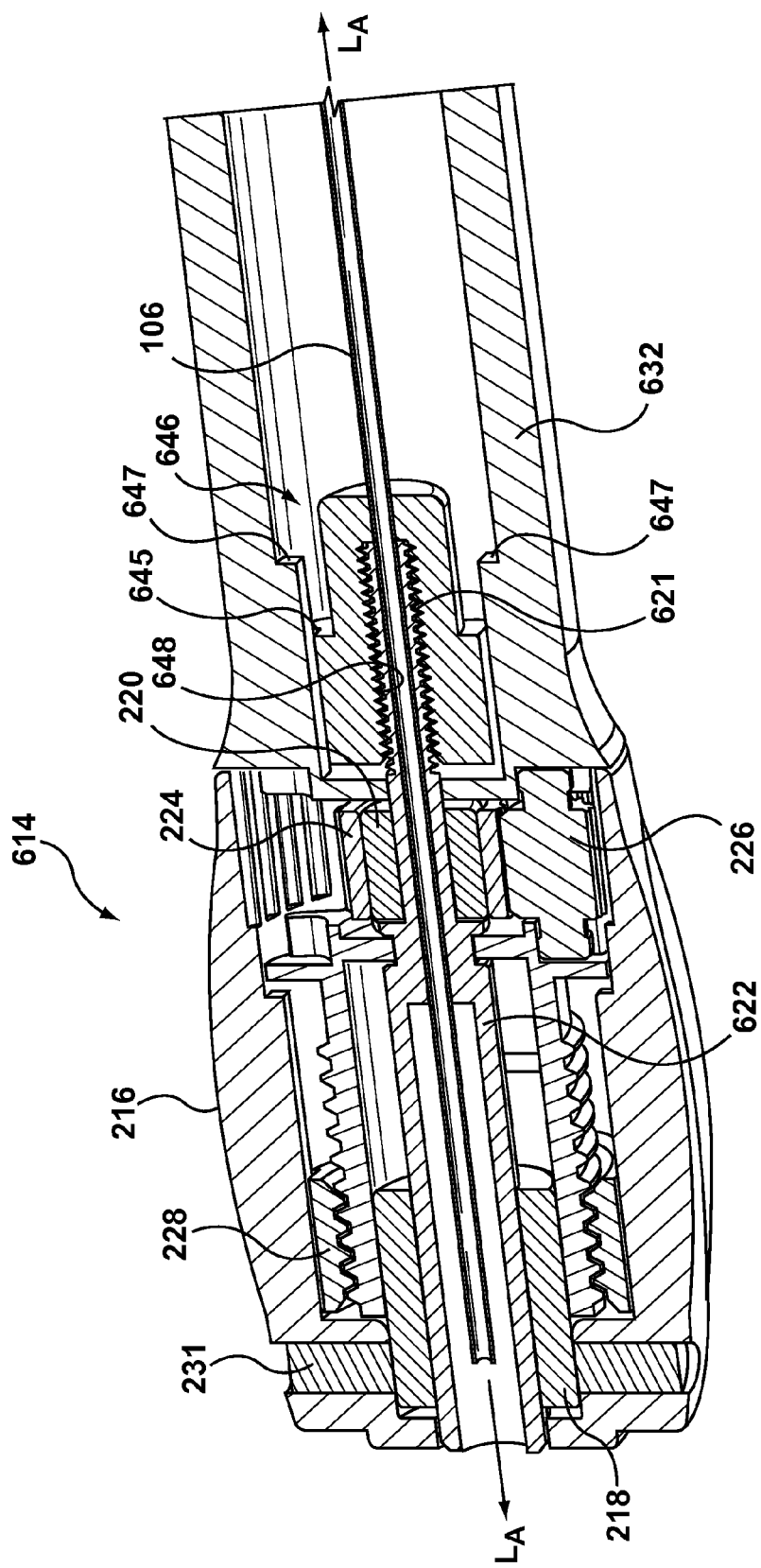
FIG. 6A is a sectional view of the tip release handle mechanism of FIG. 6 taken along line A-A thereof.

FIG. 6 depicts a perspective view in partial section of a tip release handle mechanism 614 in accordance with another embodiment hereof, and FIG. 6A is a sectional view of tip release handle mechanism 614 taken along line A-A in FIG. 6. The embodiment of FIG. 6 utilizes common components with tip release handle mechanism 114 and only components that differ in structure or function from those already described will be detailed herein. Tip release handle mechanism 614 includes rotatable grip component 216 that is operably coupled to a proximal portion of inner shaft 106 by proximal one-way bearing 218, distal one-way bearing 220, a tip release actuation component 622 having an integral, distally-extending threaded coupler 621, and first and second gears 224, 226. As well, tip release handle mechanism 614 includes stop component 228 that is longitudinally translatable by grip component 216. The mechanical interaction of the listed components of tip release handle mechanism 614 function in the same manner as in tip release handle component 114 such that when grip component 216 is rotated in each of the first and second directions, tip release actuation component 622 along with threaded coupler 621 thereof rotate in the first direction. In addition to the listed components, tip release handle mechanism 614 includes a slide component 646 operably coupled to tip release actuation component 622 by threaded coupler 621 thereof. The inner shaft 106 is secured to slide component 646 to be axially movable therewith, and includes a proximal portion that is slidably disposed within tip release actuation component 622. In an embodiment, inner shaft 106 and tip release actuation component 622 define at least a portion of a guidewire lumen of the delivery catheter. Slide component 646 includes a threaded bore 648 along a central or longitudinal axis $L_A$ thereof for receiving the complimentary threaded coupler 621 of tip release actuation component 622. Slide component 646 also includes a pair of opposing longitudinally-extending grooves or channels 645 formed in an outer surface thereof, each of which slidably engages with a complimentary longitudinally-extending rail or protrusion 647 of handle housing 632. In an embodiment, rails 647 are formed to inwardly extend from the interior surface of handle housing 632. Slide component 646 is axially translated in a distal direction along rails 647 by the rotation of tip release actuation component 622 in the first direction. More particularly when tip release actuation component 622 rotates in the first direction, threaded coupler 621 rotates in the first direction which causes threaded coupler 621 to unscrew or back out from threaded bore 648. Since tip release actuation component 622 is longitudinally fixed in position within tip release actuation mechanism 614, the rotation of threaded coupler 621 in the first direction distally advances slide component 646 and shaft component 106 that is secured thereto.

Figure 7A:
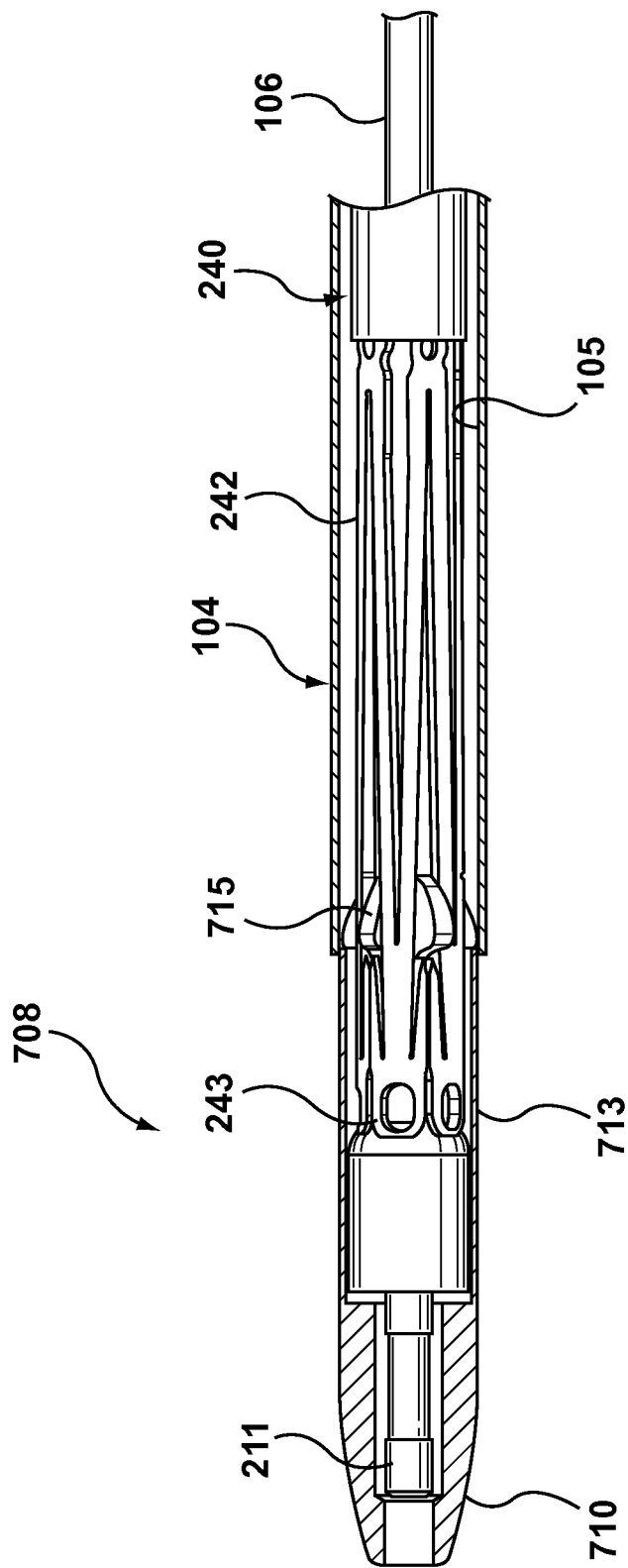
FIGS. 7A, 7B and 7C are side partial sectional views of a tip capture device for use with the tip release handle mechanism of FIGS. 6 and 6A in accordance with another embodiment hereof with a proximal stent of a stent-graft shown in a delivery state, a partially deployed state and a fully deployed state, respectively.

FIG. 7A is a sectional view of a tip capture device 708 that forms a distal tip 710 of a stent-graft delivery catheter in accordance with another embodiment hereof. Tip capture device 708 is actuatable by tip release actuation mechanism 614. Proximal stent 242 of stent-graft 240 is shown held in a compressed, delivery state by tip capture device 708 with a remainder of the stent-graft 240 being held in a delivery configuration within the lumen 105 of a distal portion of the outer shaft 104 of the delivery catheter. Proximal tips or apices 243 of proximal stent 242 are held between a sleeve 713 and a spindle 715 of tip capture device 708. Sleeve 713 is attached to distal end 211 of inner shaft 106 to axially translate therewith, such that sleeve 713 is operably coupled to inner shaft 106 to be distally advanced thereby. In an embodiment, tip release handle mechanism 614 is operably coupled to tip capture device 708 such that rotation of tip release actuation component 622 in a first direction moves or distally advances inner shaft 106 and sleeve 713 relative to spindle 715 and proximal stent 242 in two distinct steps or stages, wherein during a first step or stage the proximal tips 243 are partially uncovered and during a second step or stage the proximal tips 243 are fully uncovered and released from tip capture device 708. It would be understood by one of ordinary skill in the art that a tip capture device may incorporate other mechanisms or components than those shown in the current embodiment to transfer a translational force of shaft 106 to sleeve 713 without departing from the scope of the present invention. For example, tip capture device as shown and described in U.S. Pat. No. 8,663,302 to Schmitt et al. and U.S. Pat. No. 7,264,632 to Wright et al., each of which is incorporated by reference herein in its entirety, may be adapted for use in embodiments hereof.

Figure 7B:
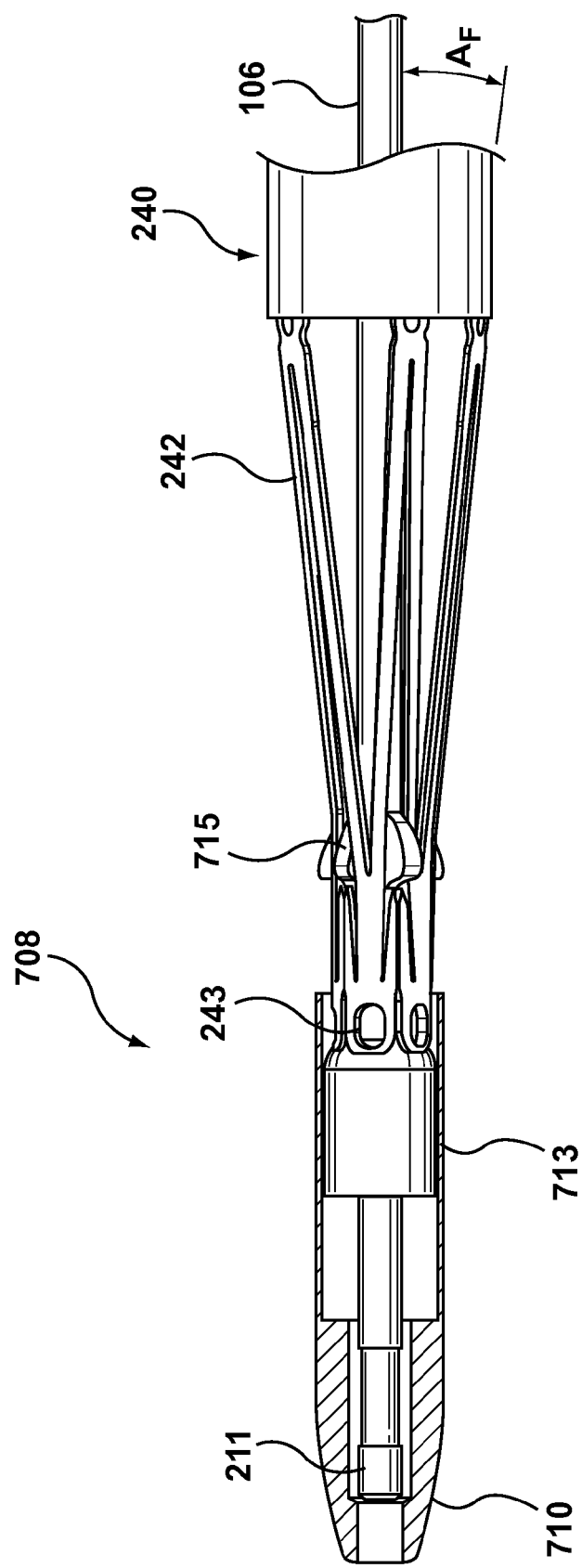
Figure 7C:
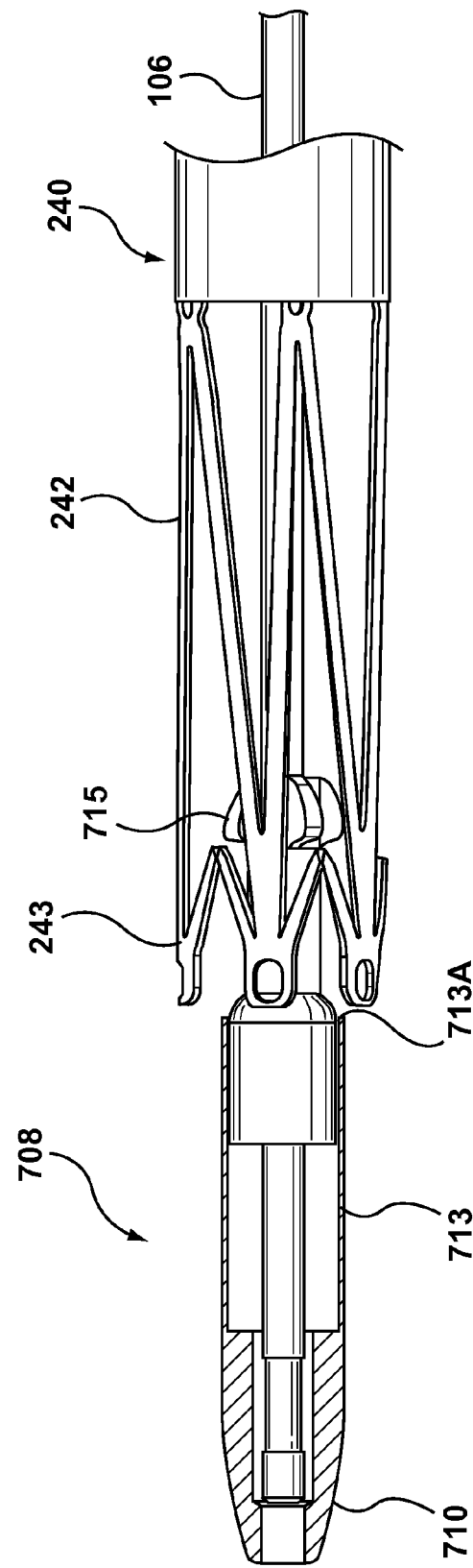

When stent-graft 240 is to be deployed from a delivery catheter in accordance with the embodiment of FIGS. 6, 7A, 7B and 7C, sheath 104 is proximally retracted a sufficient distance to uncover at least proximal stent 242 of stent-graft 240. Thereafter grip component 216 is rotated in the first direction to rotate tip release actuation component 622 in the first direction and to thereby distally advance slide component 646 and inner shaft 106, which in turn distally advances sleeve 213 to at least partially uncover proximal tips 243 of self-expanding proximal stent 242 of stent graft 240. While grip component 216 is rotated in the first direction stop component 228 is distally advanced thereby until stop component 228 contacts hard stop 230, which prevents further rotation of grip component 216 in the first direction. When grip component 216 can no longer be rotated in the first direction the first stage of tip release has been performed, wherein sleeve 713 of tip capture device 708 will have been distally advanced a sufficient distance to permit self-expanding proximal stent 242 to transition from a delivery state to a partially deployed state in which proximal tips 243 of proximal stent 242 are partially uncovered but still attached to tip capture device 708, as shown in FIG. 7B. With the proximal tips 243 partially uncovered, the remainder of the proximal stent will expand outward at an angle $A_F$ from inner shaft 106, which in embodiments hereof may be in the range of 10° to 40°. Proximal stent 106 may be described as "flowered" at this point in the procedure. With the proximal stent "flowered" in the partially deployed state, a clinician via fluoroscopy or other imaging process may assure proper positioning of proximal stent 242 and make any adjustments thereto prior to full deployment. Once proper positioning of proximal stent 242 is confirmed, the distal remainder of stent-graft 240 is fully uncovered by the continued proximal retraction of sheath 104 relative thereto and thereby releases/deploys from the delivery catheter. Grip component 216 may then be rotated in the second direction, which proximally translates stop component 228 and continues rotation of tip release actuation component 622 in the first direction to thereby resume distal advancement of slide component 622, inner shaft 106 and sleeve 713. Grip component 216 is rotated in the second direction until at least a distal edge 713A of sleeve 713 is distal of proximal tips 243 of proximal stent 242, as shown in FIG. 7C. With reference to FIG. 7C the second stage of tip release has been performed once sleeve 713 of tip capture device 708 is distal of the proximal tips 243, wherein proximal tips 243 release from or move free of tip capture device 708 and self-expanding proximal stent 242 transitions from the partially deployed state to a fully deployed state. With the release of proximal stent 242 from tip capture device 708, the stent-graft 240 is fully deployed.

Delivery catheters in accordance with embodiments hereof may be constructed to have an elongate shaft or tubular component and/or segments thereof formed of one or more polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. In other embodiments, an elongate shaft or tubular component in accordance herewith may be constructed to include a hypotube of a medical grade stainless steel or a reinforcing structure, such as a braided layer of a metallic material. In another embodiment, inner shaft 106 may be formed from nitinol.

Handle 102, tip release handle mechanisms 114, 614 and components thereof, and sheath refraction mechanism 112 and components thereof may be constructed from molded parts of suitable polymeric materials, such as polycarbonate, acrylonitrile butadiene styrene (ABS) or acetal, and/or suitable elastomeric materials. In another embodiment, tip release actuation components 222, 622 of tip release handle mechanisms 114, 614 may be made of stainless steel.

Stent-grafts that may be deployed from a delivery catheter in accordance herewith include, but are not limited to, the ENDURANT or VALIANT stent-graft products available from Medtronic, Inc. of Minneapolis, Minn.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for a stent-graft comprising:
   a tip capture device disposed at a distal end of the delivery system, wherein a proximal stent of a stent-graft is held in a delivery state by the tip capture device;
   a handle mechanism configured to deploy the proximal stent of the stent-graft, the handle mechanism having
   a grip component that is rotatable in a first direction to transition the proximal stent from the delivery state to a partially deployed state and that is rotatable in an opposite second direction to transition the proximal stent from the partially deployed state to a fully deployed state, and
   a tip release actuation component operably coupled to the grip component, wherein rotation of the grip component in each of the first and second directions rotates the tip release actuation component in the first direction; and
   a shaft component having a proximal end operably coupled to the tip release actuation component and a distal end operably coupled to the tip capture device.

2. The delivery system of claim 1, wherein the proximal end of the shaft component is secured to the tip release actuation component such that the shaft component rotates with the tip release actuation component to distally advance a sleeve of the tip capture device relative to the proximal stent of the stent-graft.

3. The delivery system of claim 2, wherein rotation of the grip component in the first direction rotates the shaft component in the first direction to distally advance the sleeve relative to the proximal stent until the proximal stent is partially uncovered and transitions from the delivery state to a partially deployed state.

4. The delivery system of claim 3, wherein rotation of the grip component in the second direction continues rotation of the shaft component in the first direction to distally advance the sleeve relative to the proximal stent until the proximal stent is released from the tip capture device and transitions from the partially deployed state to the fully deployed state.

5. The delivery system of claim 1, wherein the tip release actuation component is threadably coupled to a slide component of the handle mechanism and the proximal end of the shaft component is secured to the slide component such that rotation of the tip release actuation component in the first direction distally advances the slide component and the shaft component secured thereto to distally advance a sleeve of the tip capture device relative to the proximal stent of the stent-graft.

6. The delivery system of claim 5, wherein rotation of the grip component in the first direction distally advances the shaft component and the sleeve relative to the proximal stent until the proximal stent is partially uncovered and transitions from the delivery state to a partially deployed state.

7. The delivery system of claim 6, wherein rotation of the grip component in the second direction continues distal advancement of the shaft component and the sleeve relative to the proximal stent until the proximal stent is released from the tip capture device and transitions from the partially deployed state to the fully deployed state.

8. The delivery system of claim 1, wherein the handle mechanism further comprises:
   a proximal one-way bearing secured to a proximal portion of the tip release actuation component, and
   a distal one-way bearing secured to a distal portion of the tip release actuation component, wherein the proximal and distal one-way bearings are operably coupled to the grip component.

9. The delivery system of claim 8, wherein when the grip component is rotated in the first direction the proximal one-way bearing locks onto the tip release actuation component such that the tip release actuation component rotates in the first direction and the distal one-way bearing is idle, and wherein when the grip component is rotated in the second direction the proximal one-way bearing is idle and the distal one-way bearing locks onto the tip release actuation component such that the tip release actuation component rotates in the first direction.

10. The delivery system of claim 9, wherein the handle mechanism further comprises:
    a first gear secured to the distal one-way bearing;
    an annular gear rotatable with the grip component; and
    a second gear disposed within the handle mechanism to engage with each of the first gear and the annular gear, wherein rotation of the grip component in the second direction rotates the first gear and the distal one-way bearing in the first direction.

11. The delivery system of claim 10, wherein the annular gear extends from an inner circumferential surface of the grip component.

12. The delivery system of claim 1, wherein the handle mechanism further comprises:
    a stop component that is distally translatable relative to the grip component by rotation of the grip component in the first direction and is proximally translatable relative to the grip component by rotation of the grip component in the second direction; and
    a hard stop spaced from a proximal end of the grip component that prevents movement of the stop component in a distal direction.

13. The delivery system of claim 12, wherein when the stop component contacts the hard stop the grip component is prevented from further rotation in the first direction and the proximal stent of the stent-graft is in the partially deployed state.

14. The delivery system of claim 13, wherein when the stop component contacts the hard stop the grip component is rotatable in the second direction.

15. A delivery system for a stent-graft comprising:
a tip capture device disposed at a distal end of the delivery system, wherein a proximal stent of the stent-graft is held in a delivery state by the tip capture device; and
a handle mechanism having,
a grip component rotatable in a first direction to partially release the proximal stent from the tip capture device such that the proximal stent transitions from the delivery state to a partially deployed state, and rotatable in an opposite second direction to fully release the proximal stent from the tip capture device such that the proximal stent transitions from the partially deployed state to a fully deployed state,
a tip release actuation component for actuating the tip capture device, the tip release actuation component being operably coupled to the grip component such that rotation of the grip component in the first direction rotates the tip release actuation component in the first direction to position the tip capture device for partial release of the proximal stent and such that rotation of the grip component in the second direction rotates the tip release actuation component in the first direction to position the tip capture device for full release of the proximal stent, and
a stop component that is distally translated relative to the grip component by rotation of the grip component in the first direction and is proximally translated relative to the grip component by rotation of the grip component in the second direction, wherein when the distally translated stop component contacts a hard stop of the handle mechanism the grip component is prevented from further rotation in the first direction and the proximal stent of the stent-graft is in the partially deployed state.

16. The delivery system of claim 15, wherein the handle mechanism further comprises:
a proximal one-way bearing secured to a proximal portion of the tip release actuation component, and
a distal one-way bearing secured to a distal portion of the tip release actuation component, wherein the proximal and distal one-way bearings are operably coupled to the grip component.

17. The delivery system of claim 16, wherein when the grip component is rotated in the first direction the proximal one-way bearing locks against the tip release actuation component such that the tip release actuation component rotates in the first direction with the distal one-way bearing being idle, and when the grip component is rotated in the second direction the distal one-way bearing locks against the tip release actuation component such that the tip release actuation component rotates in the first direction with the proximal one-way bearing being idle.

18. The delivery system of claim 17, wherein the handle mechanism further comprises:
a first gear secured to the distal one-way bearing;
an annular gear rotatable with the grip component; and
a second gear disposed within the handle mechanism to engage with each of the first gear and the annular gear, wherein rotation of the grip component in the second direction rotates the first gear and the distal one-way bearing in the first direction.

19. The delivery system of claim 15, further comprising:
a shaft component having a proximal end secured to the tip release actuation component and a distal end operably coupled to the tip capture device, such that the shaft component rotates with the tip release actuation component to distally advance a sleeve of the tip capture device relative to the proximal stent of the stent-graft.

20. The delivery system of claim 15, further comprising:
the handle mechanism having a slide component that is threadably coupled to the tip release actuation component; and
a shaft component having a proximal end secured to the slide component and a distal end operably coupled to the tip capture device, wherein rotation of the tip release actuation component in the first direction distally advances the slide component and the shaft component secured thereto to distally advance a sleeve of the tip capture device relative to the proximal stent of the stent-graft.

* * * * *